(12) United States Patent
Ciomei et al.

(10) Patent No.: US 8,518,930 B2
(45) Date of Patent: *Aug. 27, 2013

(54) THERAPEUTIC COMBINATION COMPRISING A CDKS INHIBITOR AND AN ANTINEOPLASTIC AGENT

(75) Inventors: Marina Ciomei, Corsico (IT); Aurelio Marsiglio, Saronno (IT); Valter Domenico Croci, Nerviano (IT); Enrico Pesenti, Parabiago (IT)

(73) Assignee: Nerviano Medical Sciences S.r.l., Nerviano (MI) (IT)

( * ) Notice: Subject to any disclaimer, the term of this patent is extended or adjusted under 35 U.S.C. 154(b) by 191 days.

This patent is subject to a terminal disclaimer.

(21) Appl. No.: 13/055,541

(22) PCT Filed: Jul. 29, 2009

(86) PCT No.: PCT/EP2009/059815
§ 371 (c)(1),
(2), (4) Date: Jan. 24, 2011

(87) PCT Pub. No.: WO2010/012777
PCT Pub. Date: Feb. 4, 2010

(65) Prior Publication Data
US 2011/0312909 A1 Dec. 22, 2011

(30) Foreign Application Priority Data

Jul. 29, 2008 (EP) .................................. 08161320

(51) Int. Cl.
*A01N 55/02* (2006.01)
*A61K 31/555* (2006.01)

(52) U.S. Cl.
USPC ............... 514/185; 514/42; 514/43; 514/183; 514/184

(58) Field of Classification Search
None
See application file for complete search history.

(56) References Cited

U.S. PATENT DOCUMENTS
7,482,354 B2 * 1/2009 Traquandi et al. ............ 514/267

FOREIGN PATENT DOCUMENTS

| WO | WO 03/077999 A1 | 9/2003 |
|---|---|---|
| WO | WO 2004/041308 A1 | 5/2004 |
| WO | WO 2004/104007 A1 | 12/2004 |
| WO | WO 2004/110455 A1 | 12/2004 |
| WO | WO 2005/094830 A1 | 10/2005 |
| WO | WO 2007/090794 A1 | 8/2007 |

OTHER PUBLICATIONS

Socinski et al. Journal of Clinical Onocology (2006), vol. 24, pp. 4840-4847.*
Senderowicz A.M., "Small-Molecule Cyclin-Dependent Kinase Modulators", *Oncogene* 22(42):6609-6620 (2003).
Brasca M.G. et al., "Identification of N,1,4,4-Tetramethyl-8-{[4-(4-Methylpiperazin-1-yl)Phenyl]Amino}-4,5-Dihydro-1H-Pyrazolo[4,3-h]Quinazoline-3-Carboxamide (PHA-848125), a Potent, Orally Available Cyclin Dependent Kinase Inhibitor", *Journal of Medicinal Chemistry* 52(16):5152-5163 (2009).
International Search Report dated Dec. 3, 2009 received from the European Patent Office.

\* cited by examiner

*Primary Examiner* — Patrick Lewis
(74) *Attorney, Agent, or Firm* — Scully, Scott, Murphy & Presser, P.C.

(57) ABSTRACT

The present invention provides a therapeutic combination comprising (a) a compound of formula (I) as set forth in the specification and (b) one or more antineoplastic agents selected from the group consisting of alkylating or alkylating-like agents, antimetabolite agents and topoisomerase I inhibitors, wherein the active ingredients are present in each case in free form or in the form of a pharmaceutically acceptable salt or any hydrate thereof.

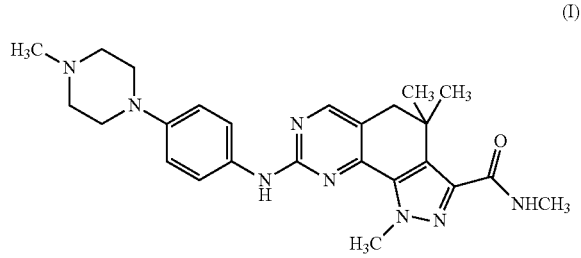

(I)

15 Claims, No Drawings

THERAPEUTIC COMBINATION COMPRISING A CDKS INHIBITOR AND AN ANTINEOPLASTIC AGENT

TECHNICAL FIELD

The present invention relates in general to the field of cancer treatment and, more particularly, provides an antitumor composition comprising a cdks inhibitor and an alkylating or alkylating-like agent and/or an antimetabolite agent and/or a topoisomerase I inhibitor, having a synergistic or additive antineoplastic effect.

BACKGROUND ART

It is well known that progression through the cell cycle is governed by a series of checkpoint controls, otherwise referred to as restriction points, which are regulated by a family of enzymes known as the cyclin-dependent kinases (cdks). In turn, the cdks themselves are regulated at many levels such as, for instance, binding to cyclins.

The coordinated activation and inactivation of different cyclin/cdk complexes is necessary for normal progression through the cell cycle. Both the critical G1-S and G2-M transitions are controlled by the activation of different cyclin/cdk activities. In G1, both cyclin D/cdk4 and cyclin E/cdk2 are thought to mediate the onset of S-phase. Progression through S-phase requires the activity of cyclin A/cdk2 whereas the activation of cyclin A/cdc2 (cdk1) and cyclin B/cdc2 are required for the onset of mitosis. For a general reference to cyclins and cyclin-dependent kinases see, for instance, Kevin R. Webster et al, in Exp. Opin. Invest. Drugs, 1998, Vol. 7(6), 865-887.

Checkpoint controls are defective in tumor cells due, in part, to disregulation of cdk activity. For example, altered expression of cyclin E and cdks has been observed in tumor cells, and deletion of the cdk inhibitor p27 KIP gene in mice has been shown to result in a higher incidence of cancer.

Increasing evidence supports the idea that the cdks are rate-limiting enzymes in cell cycle progression and, as such, represent molecular targets for therapeutic intervention. In particular, the direct inhibition of cdk/cyclin kinase activity should be helpful in restricting the unregulated proliferation of a tumor cell.

WO2007090794 (Nerviano Medical Sciences) discloses therapeutic combinations between a cdk inhibitor and monoclonal antibodies or antimitotic agents such epothilone or taxanes like docetaxel or paclitaxel. WO2004110455, WO2004041308 and WO2003077999 (Cyclacel Ltd.) relate to the combinations of a cdk inhibitor and CPT-11, gemcitabine or 5-fluorouracil respectively. WO2005094830 (Pfizer, Inc.) describes combinations of signal transduction inhibitors such as cdks inhibitors and WO2003020272 (Bristol-Myers Squibb Co.) describes combination of protein kinase inhibitors with therapeutic agents.

There is a continuous need of combination of known anticancer drugs in order to optimise the therapeutic treatment.

Some pyrazoloquinazolines have been demonstrated to be potent inhibitors of cyclin dependent kinase enzymes, particularly Cdk2. One of these compounds is currently in development as an anti-cancer agent. Cdks inhibitors are understood to block passage of cells from the G2/M phase of the cell cycle.

The present invention provides new combinations of a Cdks inhibitor with known pharmaceutical agents that are particularly suitable for the treatment of proliferative disorders, especially cancer. More specifically, the combinations of the present invention are very useful in therapy as antitumor agents and lack, in terms of both toxicity and side effects, the drawbacks associated with currently available antitumor drugs.

DESCRIPTION OF THE INVENTION

The present invention provides, in a first aspect, a therapeutic combination comprising (a) a compound of formula (I):

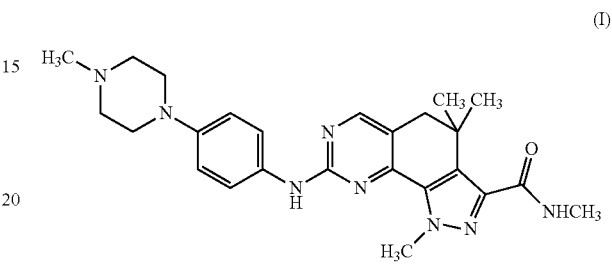

and (b) one or more antineoplastic agents selected from the group consisting of alkylating or alkylating-like agents, antimetabolite agents and topoisomerase I inhibitors, wherein the active ingredients are present in each case in free form or in the form of a pharmaceutically acceptable salt or any hydrate thereof.

The present invention also provides a combined preparation for simultaneous, separate or sequential use of the combination as described above.

In a further aspect the invention relates to the use of the combination according to the invention in a method of treating or delaying the progression of a proliferative disorder, wherein the said method comprises the simultaneous, sequential or separate administration to a subject in need thereof of the therapeutic combination.

In a still further aspect the invention provides a pharmaceutical composition comprising a combination according to the invention admixed with a pharmaceutically acceptable carrier, diluent or excipient.

A still further aspect relates to the use of a compound of formula (I) as defined above in the preparation of a medicament for the treatment of a proliferative disorder, wherein said treatment comprises simultaneously, sequentially or separately administering a compound of formula (I) as defined above and one or more antineoplastic agents selected from the group consisting of alkylating or alkylating-like agents, antimetabolite agents and topoisomerase I inhibitors, to a subject.

Another aspect relates to the use of a compound of formula (I) as defined above and one or more antineoplastic agents selected from the group consisting of alkylating or alkylating-like agents, antimetabolite agents and topoisomerase I inhibitors, in the preparation of a medicament for treating a proliferative disorder.

The compound of formula (I) has the chemical name 8-[4-(4-methyl-piperazin-1-yl)-phenylamino]-1,4,4-trimethyl-4,5-dihydro-1H-pyrazolo[4,3-h]quinazoline-3-carboxylic acid methylamide. It can be prepared as described in WO2004104007 (Pharmacia Italia SpA), is endowed with protein kinase inhibitory activity and is thus useful in therapy as antitumor agent. In particular, the preferred preparation of the compound of formula (I) is that described in example 58 of the above mentioned International Patent Application.

Pharmaceutically acceptable salts of the compound of formula (I) include the acid addition salts with inorganic or organic acids, e.g., nitric, hydrochloric, hydrobromic, sulphuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid and the like.

According to a preferred embodiment of the invention, the alkylating or alkylating-like agent is selected from the group consisting of nitrogen mustards (mechlorethamine, cyclophosphamide, ifosfamide, melphalan and chlorambucil), aziridines (thiotepa), nitrosoureas (carmustine, lomustine, semustine), triazenes (dacarbazine and temozolomide) and platinum derivatives (cisplatin, oxaliplatin, carboplatin and satraplatin). Oxaliplatin can be administered, e.g., in the form as it is marketed, e.g. under the trademark ELOXATIN®. Carboplatin can be administered, e.g., in the form as it is marketed, e.g. under the trademark PARAPLATIN®. Temozolomide can be administered, e.g., in the form as it is marketed, e.g. under the trademark TEMODAR®.

According to a more preferred embodiment of the invention, the alkylating or alkylating-like agent is temozolomide, oxaliplatin or carboplatin.

An antimetabolite agent includes, but is not limited to 5-fluorouracil, capecitabine, gemcitabine, pemetrexed, methotrexate and edatrexate. Capecitabine can be administered, e.g., in the form as it is marketed, e.g. under the trademark XELODA®. Gemcitabine can be administered, e.g., in the form as it is marketed, e.g. under the trademark GEMZAR®. Pemetrexed can be administered, e.g., in the form as it is marketed, e.g. under the trademark ALIMTA®.

A topoisomerase I inhibitor includes, but is not limited to topotecan, irinotecan, SN-38 and 9-nitrocamptothecin. Irinotecan can be administered, e.g., in the form as it is marketed, e.g. under the trademark CAMPTOSAR®. Topotecan can be administered, e.g., in the form as it is marketed, e.g. under the trademark HYCAMTIN®.

In the present invention, each of the active ingredient of the combination is in amount effective to produce a synergic antineoplastic effect.

The present invention also provides a method for lowering the side effects caused by antineoplastic therapy with an antineoplastic agent in mammals, including humans, in need thereof, the method comprising administering to said mammal a combined preparation comprising the compound of formula (I) as defined above and one or more antineoplastic agents selected from the group consisting of alkylating or alkylating-like agents, antimetabolite agents and topoisomerase I inhibitors, in amounts effective to produce a synergic antineoplastic effect.

By the term "a synergic antineoplastic effect" as used herein is meant the inhibition of the growth tumor, preferably the complete regression of the tumor, by administering an effective amount of the combination of a the compound of formula (I) as defined above and an alkylating or alkylating-like agent, an antimetabolite agents or a topoisomerase I inhibitor to mammals, including human.

The term "combined preparation" as used herein defines especially a "kit of parts" in the sense that the combination partners (a) and (b) as defined above can be dosed independently or by use of different fixed combinations with distinguished amounts of the combination partners (a) and (b), i.e. simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b). The ratio of the total amounts of the combination partner (a) to the combination partner (b) to be administered in the combined preparation can be varied, e.g. in order to cope with the needs of a patient sub-population to be treated or the needs of the single patient which different needs can be due to the particular disease, age, sex, body weight, etc. of the patients. Preferably, there is at least one beneficial effect, e.g., a mutual enhancing of the effect of the combination partners (a) and (b), in particular a synergism, e.g. a more than additive effect, additional advantageous effects, less side effects, a combined therapeutic effect in a non-effective dosage of one or both of the combination partners (a) and (b), and very preferably a strong synergism of the combination partners (a) and (b).

By the term "administered" or "administering" as used herein is meant parenteral and/or oral administration. By "parenteral" is meant intravenous, subcutaneous and intramuscolar administration.

In the method of the subject invention, for the administration of the compound of formula (I), the course of therapy generally employed is in the range from 5 mg/m$^2$ to 1.5 g/m$^2$ of body surface area. More preferably, the course therapy employed is from about 15 mg/m$^2$/day to about 200 mg/m$^2$/day of body surface area. Typical regimens comprises the following administration schedules: daily for up to 21 consecutive days; daily on days 1 to 7 of a two-weeks cycle; daily on days 1 to 4 in each of three consecutive weeks of a four-weeks cycle; daily on days 1 to 14 of a three-weeks cycle; daily on days 1 to 7 and 15 to 21 of a four-weeks cycle.

The compound of formula (I) can be administered in a variety of dosage forms, e.g., orally, in the form of tablets, capsules, sugar or film coated tablets, liquid solutions or suspensions; rectally in the form of suppositories; parenterally, e.g., intramuscularly, or through intravenous and/or intrathecal and/or intraspinal injection or infusion.

In the method of the subject invention, for the administration of an alkylating agent, preferably temozolomide, the course of therapy generally employed is from 15 mg/m$^2$ to 300 mg/m$^2$ daily. More preferably, the course of therapy generally employed is from about 50 mg/m$^2$ to 150 mg/m$^2$ daily for up to 42 consecutive days.

For the administration of a platinum derivative, preferably oxaliplatin, the course of therapy generally employed is from 10 mg/m$^2$/day to 100 mg/m$^2$/day every 2-3 weeks. More preferably, the course of therapy generally employed is from about 30 mg/m$^2$ to 85 mg/m$^2$ on day 1, once every 2 weeks.

For the administration of a platinum derivative, preferably carboplatin, the course of therapy generally employed depends on the systemic exposure (expressed as AUC value), the renal function of the patient and on the schedule of administration. A regimen targeting an AUC of from 4 to 6 mg/mL/min over a 2 to 4 week schedule is usually adopted. More preferably, a regimen targeting an AUC of 5 mg/mL/min over a 3-week schedule is used.

For the administration of an antimetabolite agent, preferably gemcitabine or pemetrexed, the course of therapy generally employed is from 200 mg/m$^2$ to 2000 mg/m$^2$ as weekly administration. More preferably, the course of therapy generally employed is from about 500 mg/m$^2$ to 1250 mg/m$^2$ on days 1 and 8 of a 21-day cycle or on days 1, 8 and 15 of a 28-day cycle or on day 1 of a 21-day cycle.

For the administration of a topoisomerase I inhibitor, preferably topotecan, the course of therapy generally employed is from 0.1 mg/m$^2$ to 2 mg/m$^2$ daily for 2-10 consecutive days.

More preferably, the course of therapy generally employed is from about 0.5 mg/m² to 1.5 mg/m² daily for 3-5 consecutive days in a 21-day cycle.

In a particularly preferred embodiment, the present invention provides a therapeutic combination comprising the compound of formula (I) as defined above, carboplatin and pemetrexed. For the administration of such combination the course of therapy generally employed is as follows. The compound of formula (I) is administered in a dose ranging from 10 to 150 mg/m²/day, preferably, 45, 60 or 80 mg/m²/day, seven days on, seven days off; pemetrexed is administered IV at a dose of 500 mg/m² over 10 minutes once every 3 weeks; carboplatin is administered 30 minutes after the end of each pemetrexed infusion once every 3 weeks, as a 30 minutes IV infusion at an AUC of 5 mg/mL/min.

The antineoplastic therapy of the present invention is in particular suitable for treating all form of cancer including, but not limited to: carcinoma such as bladder, breast, colon, kidney, liver, lung, including small cell lung cancer, oesophagus, gall-bladder, ovary, pancreas, stomach, cervix, thyroid, prostate, and skin, including squamous cell carcinoma; haematopoietic tumors of lymphoid lineage including leukaemia, acute lymphocytic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; haematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; mesothelioma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

As stated above, the effect of the combination of the invention is significantly increased without a parallel increased toxicity. In other words, the combined therapy of the present invention enhances the antitumoral effects of the partner (a) and/or of partner (b) of the combination of the invention and thus yields the most effective and less toxic treatment for tumors.

Pharmaceutical compositions according to the invention are useful in anticancer therapy.

The present invention further provides a commercial package comprising, in a suitable container mean, (a) a compound of formula (I) as defined above, and (b) one or more antineoplastic agents selected from the group consisting of alkylating or alkylating-like agents, antimetabolite agents and topoisomerase I inhibitors, wherein the active ingredients are present in each case in free form or in the form of a pharmaceutically acceptable salt or any hydrate thereof, together with instructions for simultaneous, separate or sequential use thereof.

In a package according to the invention each of partner (a) and (b) are present within a single container mean or within distinct container means.

Another embodiment of the present invention is a commercial package comprising a pharmaceutical composition or product as described above.

Due to the key role of the cdk proteins in the regulation of cellular proliferation, the combinations of the present invention are also useful in the treatment of a variety of cell proliferative disorders such as, for example, benign prostate hyperplasia, familial adenomatosis, polyposis, neurofibromatosis, psoriasis, vascular smooth cell proliferation associated with atherosclerosis, pulmonary fibrosis, arthritis, glomerulonephritis and post-surgical stenosis and restenosis.

The combinations of this invention, as modulators of apoptosis, may also be useful in the treatment of cancer, viral infections, prevention of AIDS development in HIV-infected individuals, autoimmune diseases and neurodegenerative disorders.

The activities of the combination of the present invention are shown for instance by the following in vitro and in vivo tests, which are intended to illustrate but not to limit the present invention.

EXAMPLE 1

In vitro Cytotoxic Activity of the Combination with Gemcitabine

Exponentially growing A2780 human ovarian carcinoma cells were seeded and incubated at 37° C. in a humidified 5% $CO_2$ atmosphere. After 24 hours, scalar doses of the compound of formula (I) were added to the medium for 24 hours, cells were washed and gemcitabine added for 1 hour. Cells were then washed and counted 72 hours after the first treatment. Cell proliferation was determined by a cellular adenosine triphosphate monitoring system. Cell proliferation was compared to control cells. The concentration inhibiting cell proliferation by 50% ($IC_{50}$) was calculated.

The combination indices (C.I.) were calculated using a computer program for multiple drug effect analysis based on the equation of Chou-Talalay (Adv Enzyme Regul 1984; 22:27-55) for mutually nonexclusive drugs, where a C.I. of <1 indicates a more than additive effect.

The results obtained with the drugs as single agents and in combination are shown in Table 1.

TABLE 1

| in vitro combination with gemcitabine | | |
|---|---|---|
| | $IC_{50}$ (µM) | C.I. at 90% of fraction affected |
| compound of formula (I) | 0.419 | |
| Gemcitabine | 0.364 | |
| Combination (ratio 1.25:1) | | |
| compound of formula (I) | 0.092 | 0.069 |
| gemcitabine | 0.074 | |

The results show that on human tumor cells compound of formula (I) can be effectively combined with the antimetabolite agent gemcitabine producing a more than additive (i.e. synergic) effect.

EXAMPLE 2

In vitro Cytotoxic Activity of the Combination with Oxaliplatin

Exponentially growing A2780 human ovarian carcinoma cells were seeded and incubated at 37° C. in a humidified 5% $CO_2$ atmosphere. After 24 hours, scalar doses of oxaliplatin were added to the medium for 1 hour, cells were washed and compound of formula (I) added for 24 hours. Cells were then washed and counted 72 hours after the first treatment. Cell proliferation was determined by a cellular adenosine triphosphate monitoring system. Cell proliferation was compared to control cells. The concentration inhibiting cell proliferation by 50% ($IC_{50}$) was calculated.

The combination indices (C.I.) were calculated using a computer program for multiple drug effect analysis based on the equation of Chou-Talalay (Adv Enzyme Regul 1984; 22:27-55) for mutually nonexclusive drugs, where a C.I. of <1 indicates a more than additive effect.

The results obtained with the drugs as single agents and in combination are shown in table 2.

TABLE 2 in vitro combination with oxaliplatin

| | $IC_{50}$ (µM) | C.I. at 90% of fraction affected |
|---|---|---|
| compound of formula (I) | 0.876 | |
| Oxaliplatin | 2.469 | |
| Combination (ratio 0.16:1) | | |
| compound of formula (I) | 0.081 | 0.080 |
| oxaliplatin | 0.510 | |

The results show that on human tumor cells compound of formula (I) can be effectively combined with platinum-containing compound oxaliplatin, producing a more than additive (i.e. synergic) effect.

EXAMPLE 3

In vitro Cytotoxic Activity of the Combination with SN-38

SN38 is the active metabolite of irinotecan, from which is obtained by hydrolysis. Exponentially growing A2780 human ovarian carcinoma cells were seeded and incubated at 37° C. in a humidified 5% $CO_2$ atmosphere. After 24 hours, scalar doses of SN-38 were added to the medium for 1 hour, cells were washed and compound of formula (I) added for 24 hours. Cells were then washed and counted 72 hours after the first treatment. Cell proliferation was determined by a cellular adenosine triphosphate monitoring system. Cell proliferation was compared to control cells. The concentration inhibiting cell proliferation by 50% ($IC_{50}$) was calculated.

The combination indices (C.I.) were calculated using a computer program for multiple drug effect analysis based on the equation of Chou-Talalay (Adv Enzyme Regul 1984; 22:27-55) for mutually nonexclusive drugs, where a C.I. of <1 indicates a more than additive effect.

The results obtained with the drugs as single agents and in combination are shown in table 3.

TABLE 3 in vitro combination with SN-38

| | $IC_{50}$ (µM) | C.I. at 90% of fraction affected |
|---|---|---|
| compound of formula (I) | 0.690 | |
| SN-38 | 0.039 | |
| Combination (ratio 1.6:1) | | |
| compound of formula (I) | 0.030 | 0.166 |
| SN-38 | 0.019 | |

The results show that on human tumor cells compound of formula (I) can be effectively combined with the topoisomerase I inhibitor SN-38, producing a more than additive (i.e. synergic) effect.

EXAMPLE 4

In vivo Antitumor Efficacy in Combination with Temozolomide

Balb, Nu/Nu male mice, from Harlan (Italy), were maintained in cages with paper filter cover, food and bedding sterilized and water acidified. Fragments of U87-MG human glioblastoma were implanted subcutaneously in athymic mice. This tumor model was selected because it was previously demonstrated that it is sensitive to temozolomide and also because temozolomide is the standard treatment for gliomas. The treatment with temozolomide started when tumors were palpable. Compounds were prepared immediately before treatment.

Compound of formula (I) was administrated by oral route in a volume of 10 ml/kg at the dose of 20 and 40 mg/kg twice a day (BID) for 7 consecutive days. Temozolomide was administered orally in a volume of 10 ml/kg at the dose of 25 mg/kg for 5 consecutive days. When combined, temozolomide was administered for the first 5 days and then compound of formula (I) was administered for the following 7 days. Tumor growth and body weight were measured every 3 days. Tumor growth was assessed by caliper. The two diameters were recorded and the tumor weight was calculated according the following formula: length (mm)×width$^2$/2. The effect of the antitumor treatment was evaluated as the delay in the onset of an exponential growth of the tumor (see for references, Anticancer drugs 7:437-60,1996). This delay (T-C value) was defined as the difference of time (in days) required for the treatment group (T) and the control group (C) tumors to reach a predetermined size (1 g). Toxicity was evaluated on the basis of body weigh reduction. The results were reported in table 4.

TABLE 4

In vivo efficacy in combination with temozolomide

| Treatment | T – C (days) | Tumor-free mice | Toxicity |
|---|---|---|---|
| compound of formula (I) 20 mg/kg* | 1.74 | 0/8 | 0/8 |
| compound of formula (I) 40 mg/kg* | 7.14 | 0/8 | 0/8 |
| temozolomide 25 mg/kg** | 30.88 | 1/8 | 0/8 |
| temozolomide 25 mg/kg + compound of formula (I) 20 mg/kg*** | 42.99 | 4/8 | 0/8 |
| temozolomide 25 mg/kg + compound of formula (I) 40 mg/kg*** | 34.92 | 6/8 | 0/8 |

*Treatments made orally twice at days 1-7
**Treatments made orally at days 1-5
***Temozolomide treatments on day 1-5; compound of formula (I) treatments on day 6-12

The compound of formula (I) combined with the alkylating agent temozolomide produced a clear synergic effect. The T-C observed when compound of formula (I) was combined with temozolomide was superior to the expected by the simple addition of T-C obtained by the single treatments or the number of tumor-free mice observed in the combination groups is higher than that observed with the single agents. No toxicity was observed in any of the treatment group.

EXAMPLE 5

In vivo Antitumor Efficacy in Combination with Topotecan

Balb, Nu/Nu male mice, from Harlan (Italy), were maintained in cages with paper filter cover, food and bedding sterilized and water acidified. Fragments of N-592 human small cell lung cancer tumors were implanted subcutaneously in athymic mice. This tumor model was selected because it was sensitive to topotecan and also on the basis of use of this drug in NSCL cancer.

The treatment started when tumors were palpable. Both compounds were prepared immediately before treatment.

Compound of formula (I) was administered by oral route in a volume of 10 ml/kg at the doses of 20 and 30 mg/kg twice a day (BID) for 17 days. Topotecan was administered by intravenous route in a volume of 10 ml/kg at the dose of 6 mg/kg on days 1, 5, 9, 13, 17. When combined, compound of formula (I) was administered immediately before topotecan in the days 1, 5, 9, 13, 17. Tumor growth and body weight were measured every 3 days. Tumor growth was assessed by caliper. The two diameters were recorded and the tumor weight was calculated according the following formula: length (mm)×width²/2. The effect of the antitumor treatment was evaluated as the delay in the onset of an exponential growth of the tumor (see for references Anticancer drugs 7:437-60, 1996). This delay (T-C value) was defined as the difference of time (in days) required for the treatment group (T) and the control group (C) tumors to reach a predetermined size (1 g). Toxicity was evaluated on the basis of body weigh reduction. The results are reported in table 5.

TABLE 5

In vivo efficacy in combination with topotecan

| Treatment | T – C (days) | Toxicity |
|---|---|---|
| Compound of formula (I) 20 mg/kg* | 1.61 | 0/7 |
| Compound of formula (I) 30 mg/kg* | 2.98 | 0/7 |
| topotecan 6 mg/kg** | 5.64 | 0/7 |
| Topotecan 6 mg/kg + Compound of formula (I) 20 mg/kg*** | 22.03 | 0/7 |
| Topotecan 6 mg/kg + Compound of formula (I) 30 mg/kg*** | 29.67 | 0/7 |

*Treatments made orally twice at days 1-17.
**Treatments made by intravenous route at days 1, 5, 9, 13, 17
***Days 1, 5, 9, 13, 17: docetaxel treatments, days 1-17: Compound of formula (I) treatments The compound of formula (I) combined with the topoisomerase I inhibitor topotecan produced a clear synergistic effect. The T-C observed when compound of formula (I) was combined with topotecan was highly superior to the expected by the simple addition of T-C obtained by the single treatments. No toxicity was observed in any of the treatment groups.

EXAMPLE 6

In vivo Antitumor Efficacy in Combination with 5-FU

Balb, Nu/Nu male mice, from Harlan (Italy), were maintained in cages with paper filter cover, food and bedding sterilized and water acidified. Fragments of HCT-116 human colon carcinoma were implanted subcutaneously in athymic mice. This tumor model was selected because it was sensitive to 5-FU and also on the basis of use of this drug in colon cancer.

The treatment started when tumors were palpable. Both compounds were prepared immediately before treatment.

The compound of formula (I) was administered by oral route in a volume of 10 ml/kg at the dose of 20 mg/kg twice a day (BID) for 2 cycles of 6 days. 5-FU was administered by intravenous route in a volume of 10 ml/kg at the dose of 50 mg/kg on days 1, 8. When combined, compound of formula (I) was administered starting from the day after 5-FU treatments (from day 2 to day 7 and from day 9 to day 14. Tumor growth and body weight were measured every 3 days. Tumor growth was assessed by caliper. The two diameters were recorded and the tumor weight was calculated according the following formula: length (mm)×width²/2. The effect of the antitumor treatment was evaluated as the delay in the onset of an exponential growth of the tumor (see for references Anticancer drugs 7:437-60, 1996). This delay (T-C value) was defined as the difference of time (in days) required for the treatment group (T) and the control group (C) tumors to reach a predetermined size (1 g). Toxicity was evaluated on the basis of body weigh reduction. The results were reported in table 6.

TABLE 6

In vivo efficacy in combination with 5-FU

| Treatment | T – C (days) | Toxicity |
|---|---|---|
| Compound of formula (I) 20 mg/kg* | 4.93 | 0/7 |
| 5-FU 50 mg/kg** | 2.17 | 0/7 |
| 5-FU 50 mg/kg + Compound of formula (I) 20 mg/kg*** | 10.42 | 0/7 |

*Treatments made orally twice at days 2-7 and 9-14.
**Treatments made by intravenous route at days 1, 8
***Days 1, 8: 5-FU treatments, days 2-7 and 9-14: Compound of formula (I) treatments The compound of formula (I) combined with the antimetabolite agent 5-FU produced a clear synergistic effect. The T-C observed when compound of formula (I) was combined with 5-FU was highly superior to the expected by the simple addition of T-C obtained by the single treatments. No toxicity was observed in any of the treatment groups.

The invention claimed is:

1. A therapeutic combination comprising (a) a compound of formula (I):

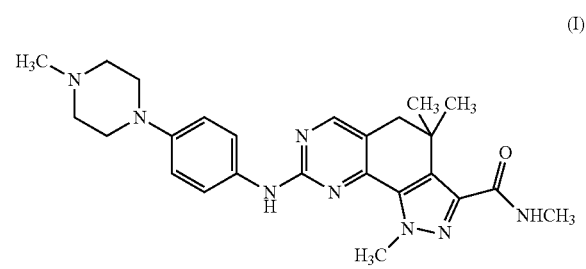 [SMILES: CNC(=O)c1nn(C)c2c1C(C)(C)Cc1cnc(Nc3ccc(N4CCN(C)CC4)cc3)nc1-2]

and (b) one or more antineoplastic agents selected from the group consisting of alkylating or alkylating-like agents, antimetabolite agents and topoisomerase I inhibitors, wherein the active ingredients are present in each case in free form or in the form of a pharmaceutically acceptable salt or any hydrate thereof.

2. A combination according to claim 1 wherein the alkylating or alkylating-like agent is selected from the group consisting of nitrogen mustards, aziridines, nitrosoureas, triazenes and platinum derivatives.

3. A combination according to claim 2 wherein the alkylating or alkylating-like agent is temozolomide, oxaliplatin or carboplatin.

4. A combination according to claim 1 wherein the antimetabolite agent is selected from the group consisting of 5-fluorouracil, capecitabine, gemcitabine, pemetrexed, methotrexate and edatrexate.

5. A combination according to claim 4 wherein the antimetabolite agent is 5-fluorouracil, gemcitabine or pemetrexed.

6. A combination according to claim 1 wherein the topoisomerase I inhibitor is selected from the group consisting of topotecan, irinotecan, SN-38 and 9-nitrocamptothecin.

7. A combination according to claim 6 wherein the topoisomerase I inhibitor is irinotecan or topotecan.

8. A combination according to claim 1 comprising the compound of formula (I) as defined in claim 1, carboplatin and pemetrexed.

9. The combination according to claim 1 which is a combined preparation for simultaneous, separate or sequential use.

10. The combination according to claim 1 in a method of treating or delaying the progression of a proliferative disorder, wherein the said method comprises the simultaneous, sequential or separate administration to a subject in need thereof of the therapeutic combination.

11. A pharmaceutical composition comprising a combination according to claim 1 admixed with a pharmaceutically acceptable carrier, diluent or excipient.

12. A method of treating a proliferative disorder in a patient in need thereof, wherein said treatment comprises simultaneously, sequentially or separately administering to said patient a compound of formula (I) as defined in claim 1 and one or more antineoplastic agents selected from the group consisting of alkylating or alkylating-like agents, antimetabolite agents or topoisomerase I inhibitors.

13. A method for treating a proliferative disorder in a patient in need thereof, comprising administering to said patient a therapeutically effective amount of the compound of formula (I) as defined in claim 1 and one or more antineoplastic agents selected from the group consisting of alkylating or alkylating-like agents, antimetabolite agents or topoisomerase I inhibitors.

14. A method for lowering the side effects caused by antineoplastic therapy with an antineoplastic agent in mammals, including humans, in need thereof, the method comprising administering to said mammal a combined preparation comprising the compound of formula (I) according to claim 1 and one or more antineoplastic agents selected from the group consisting of alkylating or alkylating-like agents, antimetabolite agents and topoisomerase I inhibitors, in amounts effective to produce a synergic antineoplastic effect.

15. A commercial package comprising, in a suitable container mean, (a) a compound of formula (I) as defined in claim 1, and (b) one or more antineoplastic agents selected from the group consisting of alkylating or alkylating-like agents, antimetabolite agents and topoisomerase I inhibitors wherein the active ingredients are present in each case in free form or in the form of a pharmaceutically acceptable salt or any hydrate thereof, together with instructions for simultaneous, separate or sequential use thereof.

* * * * *